United States Patent
Seong et al.

(10) Patent No.: US 8,445,038 B2
(45) Date of Patent: May 21, 2013

(54) **COMPOSITIONS FOR PROPHYLAXIS OR TREATMENT OF CEREBROVASCULAR DISEASES, FOR IMPROVING MEMORY IMPAIRMENT, OR FOR PROTECTING NEURONAL CELLS, CONTAINING ETHANOL EXTRACT FROM *ARALIA ELATA*, *CHAENOMELIS FRUCTUS* AND *GLYCYRRHIZAE RADIX***

(75) Inventors: Yeon Hee Seong, Cheongju-si (KR); Kyung-Sik Song, Daegu (KR); Joo Youn Kim, Seoul (KR)

(73) Assignees: Chungbuk National University Industry—Academic Cooperation Foundation, Cheongju-si (KR); Kyungpook National University Industry—Academic Cooperation Foundation, Daegu (KR)

(*) Notice: Subject to any disclaimer, the term of this patent is extended or adjusted under 35 U.S.C. 154(b) by 183 days.

(21) Appl. No.: 13/025,605

(22) Filed: Feb. 11, 2011

(65) Prior Publication Data

US 2011/0200697 A1 Aug. 18, 2011

(30) Foreign Application Priority Data

Feb. 16, 2010 (KR) .................. 10-2010-0013686

(51) Int. Cl.
*A61K 36/48* (2006.01)
*A61K 36/00* (2006.01)

(52) U.S. Cl.
USPC ............ 424/757; 424/725; 424/773; 424/777

(58) Field of Classification Search
None
See application file for complete search history.

(56) References Cited

U.S. PATENT DOCUMENTS

| | | | |
|---|---|---|---|
| 7,405,195 B2* | 7/2008 | Chen et al. | 514/18.8 |
| 2003/0143290 A1* | 7/2003 | Cho et al. | 424/728 |
| 2008/0031906 A1* | 2/2008 | Nohata et al. | 424/401 |
| 2008/0085333 A1* | 4/2008 | Hong et al. | 424/773 |
| 2008/0299159 A1* | 12/2008 | Aimi et al. | 424/401 |
| 2010/0040568 A1* | 2/2010 | Orlow et al. | 424/62 |

FOREIGN PATENT DOCUMENTS

| | | |
|---|---|---|
| KR | 1020060072642 A | 6/2006 |
| KR | 10-2008-0026266 A | 3/2008 |
| KR | 10-2009-0016883 A | 2/2009 |

OTHER PUBLICATIONS

Internet article entitled "About . . . Production Techniques to Produce Herbal Extracts", downloaded Oct. 5, 2010 from http://web.archive.org/web/20000124113842/http:/viable-herbal.com/herbology1/herbs42.htm, 5 pages, copyright 2000.*

Jung et al.; "Effects of *Chaenomelis Fructus* Extract on the Alzheimer's Disease Mice Model Induced by BA"; Korean J. Oriental Physiology & Pathology; 2004; pp. 1795-1804; vol. 18, No. 6.

Kim et al., "The Effects of *Chaenomelis fructus*,(CMF) Extract on the Alzheimer's Disease Model Induced by CT-105 and βA", J. of Oriental Neuropsychiatry, 2005, pp. 97-117, vol. 16, No. 1.

Young-Ju Yun, "Neuroprotective Effect of Palmul-Chongmyeong-Tang (PMCMT) on Ischemia-induced Learning and Memory Deficits in the Rat", Feb. 2006, 17 pages.

* cited by examiner

*Primary Examiner* — Chris R Tate
(74) *Attorney, Agent, or Firm* — The Webb Law Firm (57) ABSTRACT

Disclosed is a composition for preventing or treating cerebral infarction, cerebral edema, cerebral ischemia, or vascular dementia, for improving memory impairments, or for protecting neuronal cells, comprising as active ingredient an ethanol extract from *Aralia elata*, *Chaenomelis Fructus*, and *Glycyrrhizae Radix*.

11 Claims, 10 Drawing Sheets

Vehicle    ACG 10mg/kg    ACG 50mg/kg

FIG. 9D

COMPOSITIONS FOR PROPHYLAXIS OR TREATMENT OF CEREBROVASCULAR DISEASES, FOR IMPROVING MEMORY IMPAIRMENT, OR FOR PROTECTING NEURONAL CELLS, CONTAINING ETHANOL EXTRACT FROM *ARALIA ELATA*, *CHAENOMELIS FRUCTUS* AND *GLYCYRRHIZAE RADIX*

CROSS-REFERENCE TO RELATED APPLICATIONS

This application claims priority under 35 U.S.C. §119 to Korean Patent Application No. 10-2010-0013686, filed on Feb. 16, 2010, in the Korean Intellectual Property Office, the disclosure of which is incorporated herein by reference in its entirety.

TECHNICAL FIELD

The present invention relates to compositions for prophylaxis or treatment of cerebrovascular diseases, for improving memory impairment, or for protecting neuronal cells, and in particular, to compositions for prophylaxis or treatment of cerebral infarction, cerebral edema, cerebral ischemia, or vascular dementia, for improving memory impairment, or for protecting neuronal cells, the compositions containing an ethanol extract from *Aralia elata, Chaenomelis Fructus*, and *Glycyrrhizae Radix* as active ingredient.

BACKGROUND

Cerebral apoplexy, i.e., cerebral infarction, is caused mainly by a thrombus or embolus of the cerebral artery from arteriosclerosis and a cardiac embolism from cardiac diseases. Cerebral infarction caused by cerebrovascular occlusion is classified as cerebral thrombosis and cerebral embolism. Cerebral thrombosis refers to a pathological condition in which arteriosclerosis is caused by hypertension, diabetes, hyperlipidemia, etc., and thereby, an arterial wall becomes thick or hardened. Thus, a blood vessel becomes narrowed causing an inner wall of the blood vessel to be prone to impairment and unevenness, resulting in blood clotting and vascular occlusion. Thus, the blood supply is substantially decreased or blocked so that less oxygen and nutrients are supplied to the brain cells, resulting in cerebral dysfunction. Cerebral embolism refers to a pathological condition in which intracardiac blood flow becomes abnormal due to valvular heart disease, atrial fibrillation, etc., so some blood partially stagnates in the heart and forms clots, which are then detached and occludes a cerebral blood vessel, resulting in a cerebral infarction. Brain oxygen supply interruption over 5~6 minutes may result in irreversible cerebral change and cerebral tissue necrosis. As a result, the infract area generally experiences anemia, and gradually turns muddy brown. A part of the infract area appears to be congested and another part of the infarct area appears to have scattered petechial hemorrhage. Cerebral oxygen deficiency or blood leakage into a cerebral tissue may cause impairment of a cerebral tissue, cerebral edema, and a change in sensation and adjustment. Serious cerebral edema has a risk for increased intracranial pressure. An intracellular fluid and an extracellular fluid are primarily accumulated in the white matter. A brain with edema has many dents and becomes heavy, and thus pressurizes the ventricular system.

Degenerative cerebral disorders develop mainly by apoptosis of neuronal cells, and includes dementia, Parkinson's disease, stroke, Huntington's disease, Creutzfeldt-Jakob disease, Pick's disease, Parkinson-ALS-dementia complex of Guam, Wilson's disease, and progressive supranuclear palsy. Dementia, which is a representative degenerative cerebral disorder, is a cerebral disorder that shows a comprehensive cognitive disorder and is generally caused by a chronic or progressive cerebral disorder. It results in many higher cortical dysfunctions, such as memory, thinking, understanding, calculation, learning, language and judgment disorders. The most common cause of dementia, Alzheimer's dementia (AD), which is one of degenerative cerebral disorder, accounts for about 50 to 60%, vascular dementia (VaD) accounts for 20 to 30%, and others account for 10 to 30%. Alzheimer's dementia (AD) is a pathological condition in which a toxic substance termed Amyloid β (Aβ) is accumulated in the brain and neuronal cells are gradually killed. Clinically, it has a unique progression of very slow development and very slow worsening. The microscopic observation of brains of dead AD patients finds Aβ-accumulated characteristic senile plaque and neurofibrillary tangle. The second most common cause of dementia is vascular dementia that is caused by occlusion or stenosis of cerebral blood vessels (for example, cerebral infarction). Cerebral imaging tests such as CT or MRI find traces of cerebral blood vessel disorders, such as cerebral infarction, cerebral hemorrhages, etc., for patients with vascular dementia.

Most degenerative cerebral disorders are accompanied with dementia, in particular, a cognitive disorder and a memory disorder (memory loss). Accordingly, a therapeutic agent for degenerative cerebral disorders including dementia needs to delay destruction and aging of brain cells to protect brain cells, and recover a cognitive function. Examples of drugs developed heretofore include antioxidants, such as vitamin E and selegiline to suppress destruction of brain cells due to reactive oxygen species, and acetylcholine esterase-inhibiting drugs, such as Tacrine, Aricept, and Exelon. However, these drugs are reported to have serious side effects and low effectiveness. In addition, even healthy people experience decreased memory or concentration probably due to stress by complicated social activities and deteriorated living-environment such as pollution. In response to such problems, it is expected that a drug capable of improving memory may improve memory in people with decreased memory from a degenerative cerebral disorder, aging, or stress, and may allow patients with mental retardation to reconstruct a new memory circuit.

*Aralia elata* belonging to Araliaceae is distributed in Korea, Japan, China, etc. Shoots of *Aralia elata* collected in May and June are popular to Koreans as food. While *Aralia cordata* whose radix is called '*Aralia*' grows as a trunk from the ground, *Aralia elata* grows as a shoot and the shoot is collected. Since *Aralia elata* is a vegetable collected from the top of the head of a tree, it is also called a tree-head-vegetable or a lip-head-vegetable. *Aralia elata* is known to have antidiabetic, anti-inflammatory, analgesic, anti-oxidant, and anticancer effects. *Aralia elata* enhances viability, and is very effective for diabetics without any side effect. A bark of *Aralia elata* Seemann is referred to as Araliae Elatae Cortex. *Aralia elata* Seem in oriental medicine, and is known to be effective for neuralgia and hypertension. In addition, in oriental medicine, the *Aralia elata* Seemann bark is known to be effective for an early stage of the flu, neuralgia, and arthritis, have an ataractic effect to remove anxiety, irritation, depression, and have a unique aroma and a bitter taste for increasing appetite. *Aralia elata* contains a great amount of protein, fat, sugar, fiber, phosphorous, calcium, iron, vitamins (B1, B2, and C), and saponins to decrease blood sugar and blood lipid, and is thus effective for diabetics, nephropathy, and gastroenteric troubles. Korean Patent Publication No. 2006-0072642 discloses an agent for improving cerebral functions, containing an extract from one or two or more selected from the group consisting of *Aralia*, tree-head-vegetable, *Kalopanacis cortex*, *Phlomis umbrosa*, *Acyranthes bidentata* Blume, and *Clematis chinensis* Osbeck, in which an extract from a tree-head-vegetable inhibits β amyloid-induced toxicity on neuronal cells and memory loss caused by Scopolamine interrupting the transfer of acetylcoline. However, the published patent does not disclose a prophylactic or therapeutic effect of *Aralia elata* on cerebral infarction, cerebral edema, cerebral ischemia, or vascular dementia, and does not teach or suggest a remarkable synergic effect of *Aralia elata* in combination with other components, such as *Chaenomelis Fructus* and *Glycyrrhizae Radix*.

*Chaenomelis Fructus*, a fruit of *Chaenomeles sinensis* Koehne (Rosaceae) is known to have an antioxidant effect, an antiviral effect, etc. In addition, it is reported that *Chaenomelis Fructus* significantly suppresses β-amyloid induced memory impairment in mice, significantly improves an ischemic condition of a cerebral tissue, and suppresses ischemia-induced cerebral tissue impairment (Myeongsin Kim, et al., Journal of Oriental Neuropsychiatry, Vol. 16(1), 2005). However, its remarkable synergic effect in combination with other components, such as *Aralia elata* and *Glycyrrhizae Radix*, is not known.

Regarding *Glycyrrhizae Radix* (the root of *Glycyrrhiza uralensis* (Lycophodiaceae)), Pal-mul-chong-myeong-tang (八物聰明湯) including ginseng, *Atractylodes macrocephala* Koidzumi, white *Poria cocos* Wolf, *Glycyrrhizae Radix*, *Angelica gigas*, *Cnidium officinale*, *Rehmannia glutinosa* Liboschitz, *Paeonia japonica*, *Polygala tenuifolia*, and *Acorus gramineus* is known to be effective for suppressing memory loss and learning ability loss due to ischemia (Oriental Medical Graduate School of the Kyung Hee University, Master thesis, Yeongju-Yoon (February, 2006) "Effects of Pal-mul-chong-myeong-tang on Learning and Memorizing in Topical Prosencephalon Ischemia Animal Model."). However, effectiveness of *Glycyrrhizae Radix* alone on memory impairment, cerebral infarction, etc. has never been reported.

SUMMARY

The inventors of the present invention have tested an ethanol extract from *Aralia elata*, *Chaenomelis Fructus*, and *Glycyrrhizae Radix* for inhibitory effects on cerebral infarction and β amyloid-induced memory impairment, and found that the ethanol extract substantially suppresses cerebral infarction and edema and prevents memory impairment in an ischemic cerebral infarction-induced rat model. In addition, in order to reveal the biochemical mechanism for the pharmacological activities, the inventors cultured primary neuronal cells and found apoptosis inhibitory effects of the ethanol extract on each neurotoxic substance, and therefore, completed the present invention.

An object of the present invention is to provide compositions for prophylaxis or treatment of cerebral infarction, cerebral edema, cerebral ischemia or vascular dementia, for improving memory impairment, or for protecting neuronal cells, the compositions containing an ethanol extract from *Aralia elata*, *Chaenomelis Fructus*, and *Glycyrrhizae Radix*, as active ingredient.

The present invention provides compositions for prophylaxis or treatment of cerebral infarction, cerebral edema, cerebral ischemia or vascular dementia, for improving memory impairments, or for protecting neuronal cells, comprising an ethanol extract from *Aralia elata*, *Chaenomelis Fructus*, and *Glycyrrhizae Radix*, as active ingredient. In an embodiment of the present invention, the ethanol extract from *Aralia elata*, *Chaenomelis Fructus*, and *Glycyrrhizae Radix* may be obtained by mixing *Aralia elata*, *Chaenomelis Fructus* and *Glycyrrhizae Radix* and then extracting the mixture with ethanol, or by extracting *Aralia elata*, *Chaenomelis Fructus* and *Glycyrrhizae Radix*, separately, with ethanol, and then, mixing the extracts. Each herb or each herbal extract may be preferably used in a weight ratio of 0.5 to 2:0.5 to 2:0.5 to 2, more preferably, 1:1:1. *Aralia elata* may be used as a whole plant or an edible shoot.

DETAILED DESCRIPTION OF EMBODIMENTS

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of the exemplified embodiments. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Hereinafter, exemplary embodiments will be described in detail with reference to the accompanying drawings.

In the present invention, ethanol extracts from *Aralia elata*, *Chaenomelis Fructus* and *Glycyrrhizae Radix* are mixed to prepare a mixed extract (hereinafter referred to as 'ACG'), and an inhibitory effect of the mixed extract on ischemic cerebral infarction caused by ischemia/reperfusion as a cerebral infarction model was revealed. In addition, in order to identify the biochemical mechanism therefor, inhibitory effects on neuronal death caused by hydrogen peroxide, glutamate, an excitatory amino acid, and hypoxia in cultured neuronal cells were tested. As a result, it was revealed that ACG has excellent inhibitory effects thereon. Also, an inhibitory effect of ACG on memory impairments caused by intraventricular injection of Aβ(25-35) in a mouse as a memory impairment model was revealed, and as the biochemical mechanism therefor, it was also revealed that ACG suppressed apoptotic cell death of cultured neuronal cells caused by Aβ(25-35). Such results show that ACG can be used as a prophylactic or therapeutic agent for degenerative cerebral disorders including dementia and a stroke.

In particular, the three components have a specific inhibitory effect, not a non-specific inhibitory effect. That is, the three components selectively inhibit toxicity according to the kind of toxic substances. That is, while *Aralia elata* and *Glycyrrhizae Radix* inhibit hydrogen peroxide-induced cytotoxicity at a very high concentration, and *Chaenomelis Fructus* does not inhibit it at all, ACG shows a high inhibitory effect thereon. While only *Aralia elata* has a low inhibitory effect on glutamate-induced toxicity, ACG shows a high inhibitory effect thereon. While only *Glycyrrhizae Radix* has a high inhibitory effect on hypoxia-induced toxicity, ACG also shows a high inhibitory effect thereon. This shows that *Aralia elata*, *Chaenomelis Fructus*, and *Glycyrrhizae Radix* have complementary actions by supplementing a mechanism deficient to the other components one another, and due to the complementary actions, it is considered that ACG has a remarkable synergic effect. In addition, regarding Aβ-induced cytotoxicity, although all the components have a considerable inhibitory effect, *Aralia elata* and *Chaenomelis Fructus* show toxicity at a dose of 10 μg/ml or more. By contrast, it was confirmed that ACG shows a high inhibitory effect in a dose-dependent manner up to a dose of 50 μg/ml. This suggests that ACG shows an excellent effect safely without any side effect, by employing a relatively small amount based on the amount of each component. Therefore, ACG can protect neuronal cells in a more effective manner, and can prevent and treat cerebral infarction, cerebral edema, cerebral ischemia, and vascular dementia, and improve memory impairment, in a more effective manner, without any side effect.

In the present invention, *Aralia elata*, *Chaenomelis Fructus*, and *Glycyrrhizae Radix* are mixed and the mixture is extracted with ethanol to obtain a mixed extract. Alternatively, each of *Aralia elata*, *Chaenomelis Fructus*, and *Glycyrrhizae Radix* is extracted with ethanol to obtain extracts, and then the extracts are mixed together to obtain the mixed extract. Each herb or herbal extract may be preferably used in a weight ratio of 0.5 to 2:0.5 to 2:0.5 to 2, more preferably, 1:1:1. Within the weight ratio ranges, the extract has high prophylactic and therapeutic effects on cerebral infarction, cerebral edema, cerebral ischemia and vascular dementia, and a high memory impairment improving effect. In a preferable embodiment, *Aralia elata* is used as a whole plant.

When a prophylactic or therapeutic agent for cerebral infarction or memory impairment according to the present invention is manufactured into a pharmaceutical formulation, the active ingredient may be combined with one or more conventional pharmaceutically acceptable carriers, and then, manufactured into either an orally administrable formulation, such as tablets, hard or soft capsules, chewable tablets, powder, liquid or suspension, or a parenteral formulation, such as an injectable liquid or suspension, or a intranasal formulation, depending upon administration purpose.

When the active ingredient according to the present invention is prepared in a tablet, a hard or soft capsule, a chewable tablet, powder, liquid or suspension, etc., for the purpose of oral administration, the active ingredient may be used in combination with a binder, such as Gummi Arabicum, corn starch, micro-crystalline cellulose, or gelatin; an excipient, such as dicalcium phosphate or lactose; a disintegrant, such as an alginic acid, corn starch, or a potato starch; a lubricant, such as magnesium stearate; a sweetening agent, such as sucrose or saccharine; and a flavoring agent, such as peppermint, methyl salicylate, or fruit favors. For a capsule as unit dosage form, a liquid carrier, such as polyethylene glycol or fatty oil, may be further used in combination of the components described above.

Also, a parenteral formulation, such as injectable liquid or suspension, may be administered parenterally, for example, subcutaneously, intravenously, intramuscularly, or intraperitoneally. Generally, an injectable liquid or suspension may be prepared by homogeneously mixing an effective amount of active ingredient in a pharmaceutically acceptable liquid carrier such as water, saline, aqueous dextrose and related sugar solution, non-volatile oil, ethanol, glycerin, or glycol such as polyethylene glycol or propylene glycol. Besides, if necessary, an auxiliary, such as a solubilizing agent, an antibacterial agent, a chelating agent, a buffer, or a preservative, may be further used in combination.

The pharmaceutically acceptable carrier may be any one of various auxiliaries, as long as it is pharmaceutically inert and substantially non-toxic, and does not have adverse effect on activities of active ingredient.

The ethanol extract from *Aralia elata*, *Chaenomelis Fructus*, and *Glycyrrhizae Radix* according to the present invention is a natural extract and at any concentration, does not cause specific symptoms in animal tests. That is, the ethanol extract is non-toxic to the body and does not cause any side effect. Accordingly, in addition to the pharmaceutical formulations described above, the prophylactic or therapeutic agent according to the present invention may be further used in an appropriate amount in conventional drinks such as soft drinks, mineral water or an alcoholic beverage, a chewable gum, a caramel product, candy, ice cream, a snack, a health supplement food product including vitamin or mineral. In addition, the prophylactic or therapeutic agent according to the present invention may be included in a food additive so as to be manufactured in the form of a food product or a food supplement.

A daily dose of the prophylactic or therapeutic agent according to the present invention may be varied according to seriousness of a disease, complications, weight, age, and gender of a subject to be administered. For example, in general, the daily dose of the mixed extract may be in a range of 1 to 1,000 mg/kg, preferably 10 to 500 mg/kg, more preferably 10 to 100 mg/kg. It may be orally administered once or three times a day.

Hereinafter, the present invention will be described in more detail with reference to the following examples, which are provided only for illustrative purpose but not intended to limit the scope of the present invention in any manner.

EXAMPLE 1

Preparation of Ethanol Extract from Aralia elata, Chaenomelis Fructus, and Glycyrrhizae Radix A sample (sample number: KNUNPC-AE-09-001) which had been grown and collected in an area near Sang-ju in Gyong Sang-buk-do in March through May 2009, and identified and stored by Natural Material Chemistry Laboratory at Kyungpook National University was used as *Aralia elata*. *Aralia elata* was dried in a well-ventilated dark place, followed by extracting three times with 95% ethanol from 3.12 kg of dried *Aralia elata* at a temperature of 78° C. for 3 hours. The solutions were combined, and filtered and concentrated under reduced pressure using a rotary evaporator, to obtain an ethanol-soluble component.

A sample (sample number: KNUNPC-CF-09-001) that had been obtained in a herbal market in Daegu-si in September 2009, and identified and stored by Natural Material Chemistry Laboratory at Kyungpook National University was used as *Chaenomelis Fructus*. Dried *Chaenomelis Fructus* of 2.7 kg was extracted three times with 95% ethanol at a temperature of 78° C. for 3 hours. The solutions were combined, and filtered and concentrated under reduced pressure using a rotary evaporator, to obtain an ethanol-soluble component.

A sample (sample number: KNUNPC-GR-06-001) which had been obtained from a herbal market in Daegu-si, and identified and stored by Natural Material Chemistry Laboratory at Kyungpook National University was used as *Glycyrrhizae Radix*. 4 kg of dried *Glycyrrhizae Radix* was chopped and extracted with 95% ethanol three times in a water bath using a reflux evaporator for 3 hours. The solutions were combined, and filtered and concentrated under reduced pressure using a rotary evaporator, to obtain an ethanol-soluble component.

The three kinds of extracts were mixed in a weight ratio of 1:1:1 to prepare a mixed extract (ACG).

EXAMPLE 2

Preparation of Hard Capsules

| | |
|---|---|
| 10X concentrate of the mixed extract of Example 1 | 10 mg |
| D-sorbitol | 10 mg |
| Lactose | 5 mg |
| Colloidal silicon dioxide | 5 mg |
| Magnesium stearate | 3 mg |
| Total | 33 mg |

The components were mixed in the amounts described above, and hard gelatin capsules with appropriate sizes were then filled with the mixture such that each capsule contained 33 mg of the mixture, according to a conventional method, to obtain the desired capsules.

EXAMPLE 3

Preparation of Tablets

| | |
|---|---|
| 10X concentrate of the mixed extract of Example 1 | 10 mg |
| D-sorbitol | 10 mg |
| Lactose | 5 mg |
| Colloidal silicon dioxide | 5 mg |
| Magnesium stearate | 3 mg |
| Total | 33 mg |

The components were mixed in the amounts described above, and then tablets were prepared according to a conventional method.

EXAMPLE 4

Preparation of Soft Capsules

| | |
|---|---|
| 10X concentrate of the mixed extract of Example 1 | 10 mg |
| Soybean oil | 100 mg |
| Palm oil | 76 mg |
| Total | 186 mg |

The components were mixed in the amounts described above, and then soft capsules were prepared according to a conventional method.

EXAMPLE 5

Preparation of Injectable Solution

| | |
|---|---|
| 10X concentrate of the mixed extract of Example 1 | 10 mg |
| Tocopherol | 172 mg |
| Selenium | 30 mg |
| Distilled water for injection | q.s. |
| pH adjusting agent | q.s. |

In one vial (10 cc) for injection, the injectable solution was prepared from the components described above according to a conventional method.

EXPERIMENTAL EXAMPLE 1

Evaluation of Inhibitory Effect of ACG on Cerebral Infarction Following Ischemia/Reperfusion by Middle Cerebral Artery Occlusion (MCAO)

300±5 g of Sprague-Dawley (SD) rats were inhalation-anesthetized with 1-2% isofluran ($N_2O:O_2$=4:1), and the right carotid artery was carefully exposed by surgical operation. The occipital artery branched from the external carotid artery to the central portion and the thyroid gland artery branched from the external carotid artery to the internal carotid artery were occluded by electrocautery. The surrounding was arranged until a Y-shaped branch was identified above the internal carotid artery, and then a head part of the external carotid artery was tied up with a thread to block the blood flow and upper and lower portions were nipped with clips so as to block the blood flow between the common carotid artery and the internal carotid artery. Then, a small pore was formed in the common carotid artery and a probe was inserted therethrough, and then a portion below the probe and the external carotid artery was tied up with a thread to such a level that hemorrhage did not occur. Then, the clips for blocking the flow of blood were removed. The pore through which the probe was inserted was cut and separated from the tied-up portion of the external carotid artery and then, the probe inserted into the external carotid artery was carefully inserted toward the internal carotid artery. The probe was inserted into an inner blood vessel from among blood vessels branched into a Y-shape above the internal carotid artery. The probe was inserted from the common carotid artery branch by 20 mm. A rectal temperature was measured immediately after surgery and then, the temperature was maintained at 37±0.5° C. using a heating pad for 6 hours. After two-hour occlusion, the probe was removed to perform reperfusion. After 24 hours, rats were killed by decapitation with anesthesia with diethyl ether. Then, brains were isolated from the rats and bone matrix was cut at a thickness of 2 mm, and then stained with 2% TTC (2,3,5-triphenyltetrazolium chloride) solution at a temperature of 37° C. for 30 minutes and was photographed using a digital camera. Then, infarct volume and edema volume were measured from the photographs by using an image analysis system.

Infarct volume=[(right normal tissue volume−left normal tissue volume)/right normal tissue volume]×100

Figure 1:
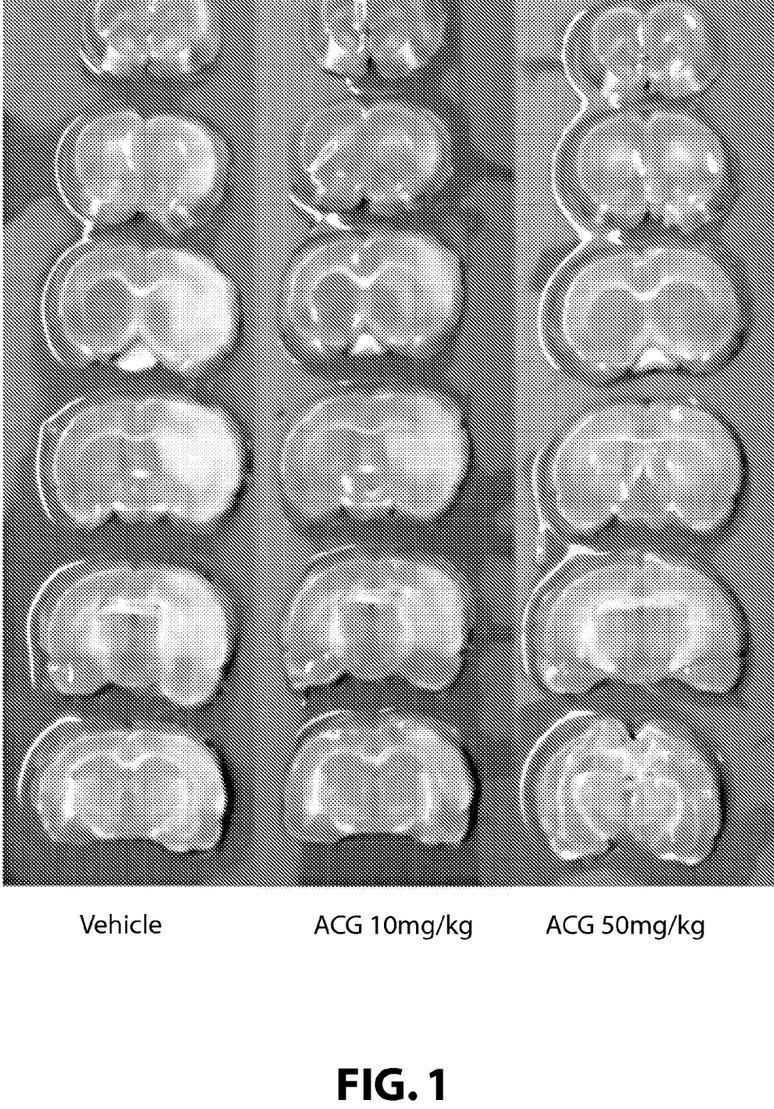
FIG. 1 shows an image showing an inhibitory effect of mixed extracts (ACG) including *Aralia elata* extract, *Chaenomelis Fructus* extract and *Glycyrrhizae Radix* extract on cerebral infarction induced by occlusion/reperfusion.
Figure 2:
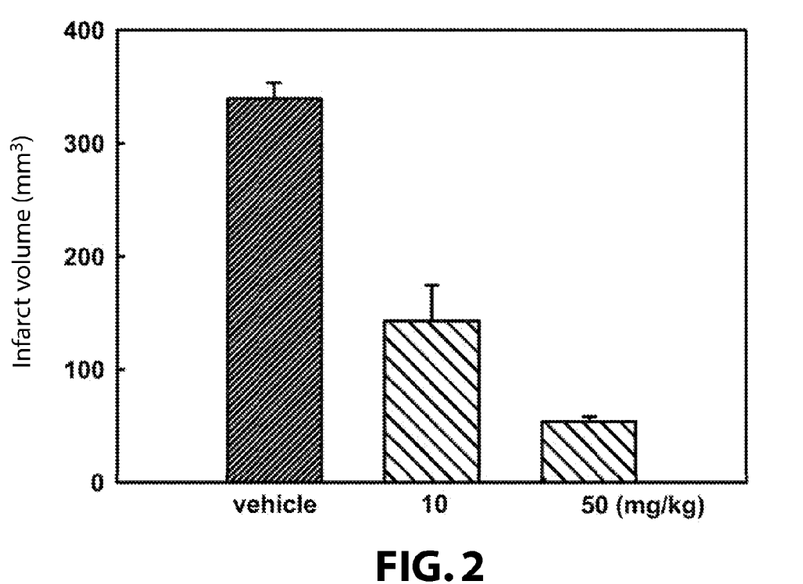
FIG. 2 is a graph showing an inhibitory effect of mixed extracts (ACG) including *Aralia elata* extract, *Chaenomelis Fructus* extract and *Glycyrrhizae Radix* extract on cerebral infarction.
Figure 3:
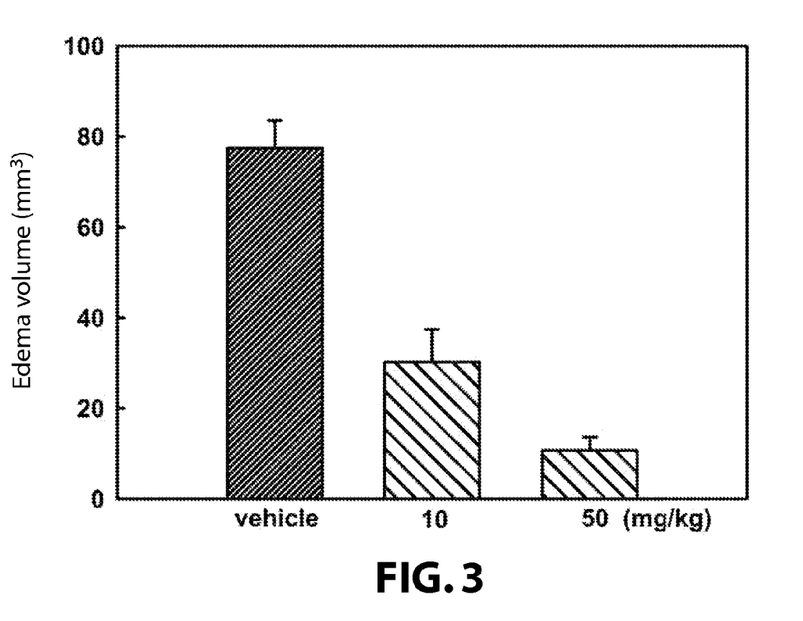
FIG. 3 is a graph showing an inhibitory effect of mixed extracts (ACG) including *Aralia elata* extract, *Chaenomelis Fructus* extract and *Glycyrrhizae Radix* extract on cerebral edema.

The results are shown in FIGS. 1 through 3.

Referring to FIG. 1, the left image is of a cerebral tissue of a non-treated rat in which cerebral ischemia was developed as a white region, and the middle image is of a cerebral tissue of a rat orally administered with 10 mg/kg of ACG 30 minutes before and one hour after the artery occlusion, and one hour after the removal of occlusion, and the right image is of a cerebral tissue of a rat orally administered with 50 mg/kg of ACG 30 minutes before and one hour after the artery occlusion, and one hour after the removal of occlusion. From the results, it was confirmed that ACG substantially inhibited cerebral infarction from cerebral ischemia induced by carotid artery occlusion Furthermore, as shown in FIG. 2, the control group has an infarct volume of 339.7 mm$^3$, and the group treated with 10 mg/kg of ACG has an infarct volume of 142.9 mm$^3$, and the group treated with 50 mg/kg of ACG has an infarct volume of 53.9 mm$^3$. Thus, it is confirmed that ACG suppresses cerebral infarction in a dose-dependent manner.

Still Furthermore, as shown in FIG. 3, the control group has a cerebral edema volume of 77.4 mm$^3$, the group treated with 10 mg/kg of ACG has a cerebral edema volume of 30.2 mm$^3$, and the group treated with 50 mg/kg of ACG has a cerebral edema volume of 10.7 mm$^3$. Thus, it is confirmed that ACG suppresses cerebral edema in a dose-dependent manner.

In conclusion, ACG substantially decreases an infarct volume and an edema volume of a rat cerebral tissue having infarction induced by ischemia/reperfusion.

EXPERIMENTAL EXAMPLE 2

Evaluation of Memory and Learning by Passive Avoidance Test (Step-Through Method)

A passive avoidance test is one of generally available and excellent test methods for rodents among methods of evaluating effects of a drug on memory and learning. A step-through apparatus (Gemini II avoidance system, San Diego Instrument) used was a shuttle box divided into two compartments (25(W)×21(D)×19(H) cm), the compartments being connected through a photo cell-guarded gate, and having a bottom of grids. One compartment was set to be bright using a lamp and the other compartment connected thereto through the gate was set to be dark, and an electric pulse was applied through grids of the dark compartment.

Animals used were ICR mice, which were acclimated for a certain period of time after the purchase. On the first experimental day (0 day), the mice were orally administered with ACG (10, 25, and 50 mg/kg), and after 30 minutes, 15 µl (15 nmol) of 1 mM Aβ(25-35) was slowly injected to the ventricle using a microsyringe equipped with a needle of 27 gage. Then, for one week, the mice were administered with ACG once a day and were placed in the bright side to be adapted to both compartments. This adaptation test was repeated at least three times. On the seventh day, the mice were orally administered with ACG and after 30 minutes, placed in the bright side and after 10 seconds, the gate was opened to allow the mice to enter the dark side. Once the mice moved to the dark side, the gate was closed and an electric pulse of 0.2 mA was applied for 2 seconds. By this test, the mice would acquire the memory for electric shock in the dark side. After 24 hours, when the mice were placed in the bright side and the above procedure was repeated, it would remember the electric shock before 24 hours and would not move into the dark side. The latency time in the bright side was measured and used as an index to evaluate formation of memory, and 5 or more minutes of latency time were set to be 5 minutes.

Figure 4A:
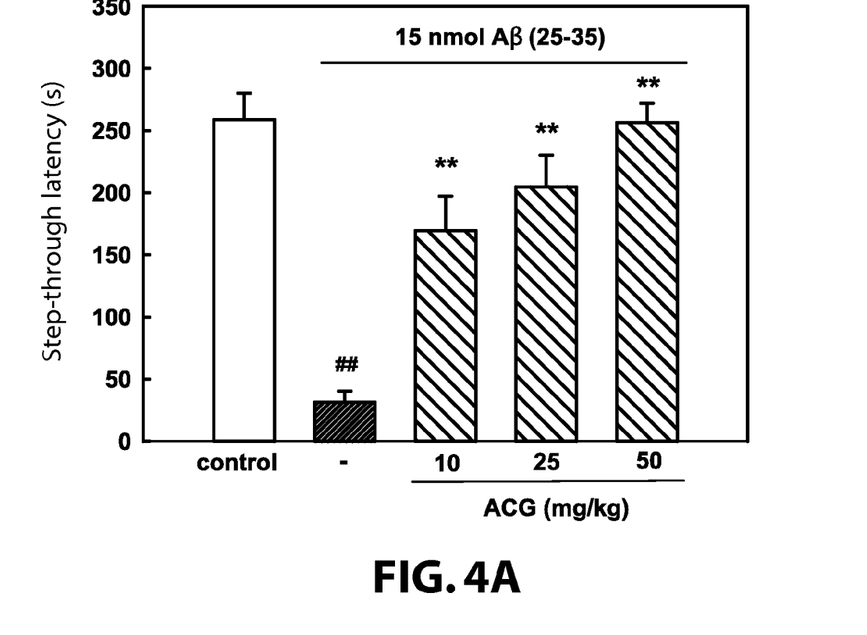
FIG. 4 is a graph showing inhibitory effects of (A) *Aralia elata*, *Chaenomelis Fructus* and *Glycyrrhizae Radix* extract (ACG) and (B) *Chaenomelis Fructus* extract (CS) on Aβ (25-35)-induced memory impairment in a passive avoidance test.
Figure 4B:
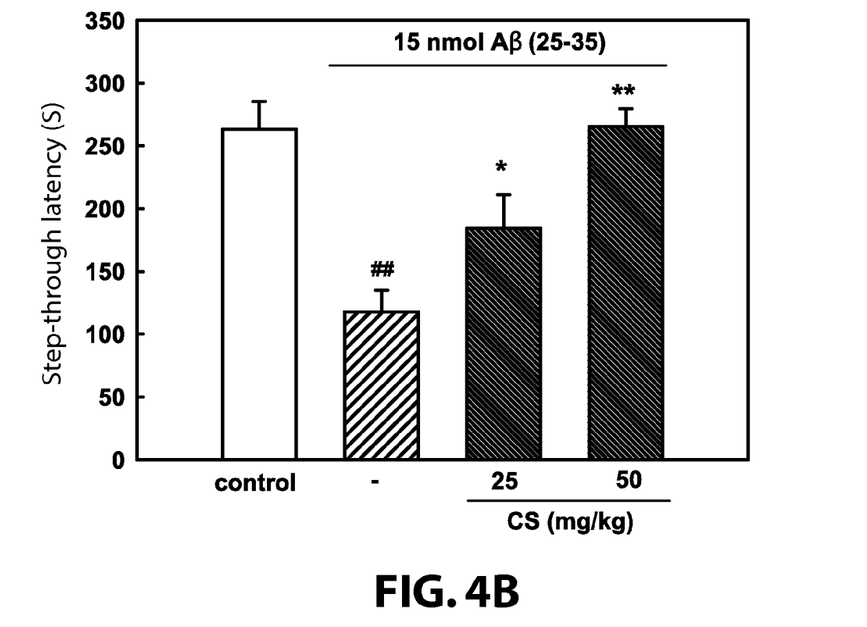

The results are shown in FIG. 4. Referring to FIG. 4(A), when Aβ(25-35) (15 nmol) was administered to the ventricle and a passive avoidance test was performed one week after the administration of Aβ(25-35), the control group that was not treated with Aβ(25-35) moved to the dark side at 259 seconds and the group administered with Aβ(25-35) was moved to the dark side at 32 seconds. This shows that memory was not formed in the group administered with Aβ(25-35). In contrast, the groups administered with 10, 25 and 50 mg/kg of ACG every day for one week showed the latency times increased in a dose-dependent manner. For example, the latency time of the group administered with 10 mg/kg of ACG was 169 seconds, the latency time of the group administered with 25 mg/kg of ACG was 205 seconds, and the latency time of the group administered with 50 mg/kg of ACG was 256 seconds. That is, the latency times of all the treated groups significantly increased and thus, it was confirmed that ACG suppressed memory impairment induced by Aβ(25-35). Meanwhile, as a result of testing each component for its effect to inhibit memory impairment, only *Chaenomelis Fructus* substantially inhibited memory impairment upon administration at a concentration of 25 and 50 mg/kg (see (B) of FIG. 4). Such results show that *Chaenomelis Fructus*, in combination with *Aralia elata* and *Glycyrrhizae Radix* having no inhibitory effect on memory impairment separately, has an increased inhibitory effect on memory impairment such that the ACG extract at a dose equal to or lower than that of *Chaenomelis Fructus* extract based on the total amount of the extract has a remarkably high inhibitory effect on memory impairment, comparable to that of *Chaenomelis Fructus* extract. Thus, it was confirmed that by using the combination of *Chaenomelis Fructus* extract with *Aralia elata* extract and *Glycyrrhizae Radix* extract having no memory impairment inhibitory effect separately, a high memory impairment inhibitory effect was achieved using a much smaller amount of *Chaenomelis Fructus* extract.

EXPERIMENTAL EXAMPLE 3

Evaluation of Memory and Learning by Water Maze Test

A round water tank with a diameter of 90 cm and a depth of 40 cm was divided into four sections and a platform with a height of 20 cm was installed in one of the sections. The temperature of water was 20° C. and the tank was filled with water until the water level was higher than the platform by 1.5 cm. Then, whole milk powder was added to the water to make the water be opaque, thereby shielding the platform from the water surface. The mice were arbitrarily divided into groups and each group was allowed to start swimming from each section to search for the platform. This test was performed once per section at a time interval of one hour from one to another section for four sections to measure the swimming time (preliminary value). The maximum swimming time was set 2 minutes and if a mouse failed to find the platform, the mouse was artificially placed on the platform for one hour. In the following day, as in Experimental Example 2, 15 nmol of Aβ(25-35) was administered into the ventricle of the mice and a control group was administered with sterilized physiological saline. ACG was orally administered once a day from the day on which Aβ(25-35) was administered to the day on which the water maze test was finished. From the fifth day from the Aβ(25-35) administration, a time required for each mouse to find the platform was measured four times at a time interval of one hour every day for 5 days (indicated as from the first day to the fifth day) in the same method as in the preliminary test, and the mean time (latency time) was measured to evaluate a degree of memory formation.

Figure 5:
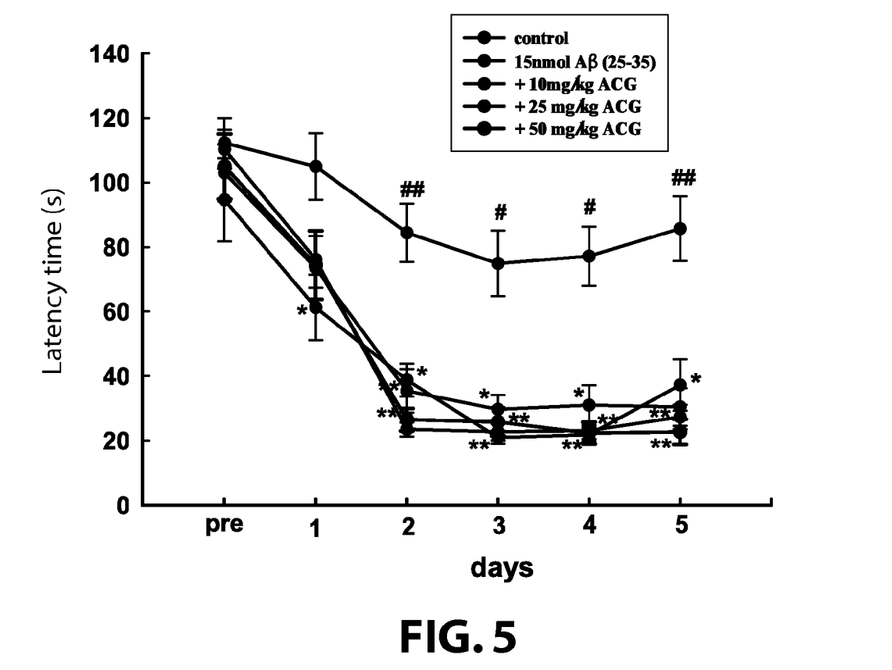
FIG. 5 is a graph showing inhibitory effects of *Aralia elata*, *Chaenomelis Fructus* and *Glycyrrhizae Radix* extract (ACG) on memory impairment in a water maze test.

The results are shown in FIG. 5. As shown in FIG. 5, regarding all the groups, the latency time before administration of Aβ(25-35) (15 nmol) (0 day) was compared to the latency time on the $5^{th}$ day after the administration. The latency time of the control group was reduced from 110.3 seconds to 27.3 seconds, which indicates the formation of memory. In contrast, the group administered with only Aβ(25-35) showed the latency time changed from 112.2 seconds to 85.7 seconds, which indicates the non-formation of memory. Meanwhile, among the groups orally administered with ACG for 5 days, the group administered with 10 mg/kg of ACG showed the latency time changed from 103.0 seconds to 30.4 seconds, the group administered with 25 mg/kg of ACG showed the latency time changed from 94.6 seconds to 37.2 seconds, and the group administered with 50 mg/kg of ACG showed the latency time changed from 105.0 seconds to 22.7 seconds. Thus, all the administration groups indicated the formation of memory. Therefrom, it could be confirmed that ACG suppressed memory impairment induced by Aβ(25-35).

EXPERIMENTAL EXAMPLE 4

Evaluation of Inhibitory Effect on Neuronal Death—MTT Colorimetric Assay (1) Culture of Cerebral Cortex Neuronal Cells A fetus rat was separated from a 15-day pregnant rat, and only a cerebral cortex was isolated therefrom under a microscope. The cerebral cortex was added to trypsin (0.25 mg/ml)-containing Joklik-modified Eagle's medium and mechanically dispersed using a 5 ml pipette. It was cultured at a temperature of 37° C. for 10 minutes to perform enzymatic degradation. A cell suspension was centrifuged at 1,500 rpm for 5 minutes to obtain a cell-containing precipitation layer. Thereto was added a DMEM supplemented with sodium bicarbonate (44 mM), penicillin (40 U/ml), gentamicin (50 g/ml), KCl (5 mM) and 10% fetal bovine serum (FBS) to adjust a cell concentration to be $2 \times 10^6$ cells/ml. It was passed through a nylon mesh (35 μm) and seeded on a poly-L-lysine coated container for incubation. The culture was performed in a $CO_2$ incubator at a temperature of 37° C. under 5% $CO_2$/95% air.

(2) Culture of Cerebellum Granule Cells

Cerebellum granule cells were isolated from a 7 to 8-day aged SD rat, and as the culture of the cerebral cortex neuronal cells, the cells were cultured in the FBS-DMEM medium having the concentration of FBS maintained at 10%. On the second day after seeding, the medium was replaced with 20 μM cytosine arabinoside-containing FBS-DMEM medium and cultured, and the test was performed on 7~10 days from the culture.

(3) MTT Assay (Measurement of the Number of Viable Cells)

In order to identify a mechanism for an inhibitory effect of ACG on cerebral infarction, the cultured brain cells used in the experiment (1) were used herein. In all tests, cell viability was measured by MTT (3-[4,5-dimethylthiazol-2-yl]-2,5-diphenyl-tetrazolium bromide) assay. This assay is a very sensitive and stable method of measuring viability and proliferation of cells quantitatively, and is based on an activity of mitochondria that converts yellow aqueous substrate MTT into dark blue formazan in a viable cell. Accordingly, the amount of generated formazan is proportional to the number of viable cells, and a higher absorption means a larger number of viable cells.

The neurons treated with toxicants for a given time after the drug treatment was deprived of the medium, and thereto was an MTT (0.5 mg/ml) solution, followed by 4-hour incubation at a temperature of 37° C. Then, the MTT solution was removed and 200 μl of acidic isopropanol (0.04 N HCl in isopropanol) was added to all the wells to dissolve generated dark blue formazan crystals, and absorbance was measured using a microelisa reader at a wavelength of 570 nm (reference wavelength of 630 nm). The absorbance of the group not treated with the drug, as a control group, was set as 100%, and the absorbance of the groups treated with $H_2O_2$, glutamate, hypoxia and Aβ(25-35), respectively, and treated with ACG together with $H_2O_2$, glutamate, hypoxia and Aβ(25-35), respectively, was represented as % of the control group.

(4) Inhibitory Effect on Hydrogen Peroxide-Induced Neuronal Death

In order to explain ischemic cerebral impairments, hydrogen peroxide ($H_2O_2$) (100 μM) was added to the cultured cerebral cortex neuronal cells for 15 minutes, washed, and then, incubated in $H_2O_2$-free and FBS-free media for 12 hours to apply oxidative stress to the cells, to investigate an inhibitory effect of ACG on apoptosis of the cultured neuronal cells in the experiment (1).

Figure 6A:
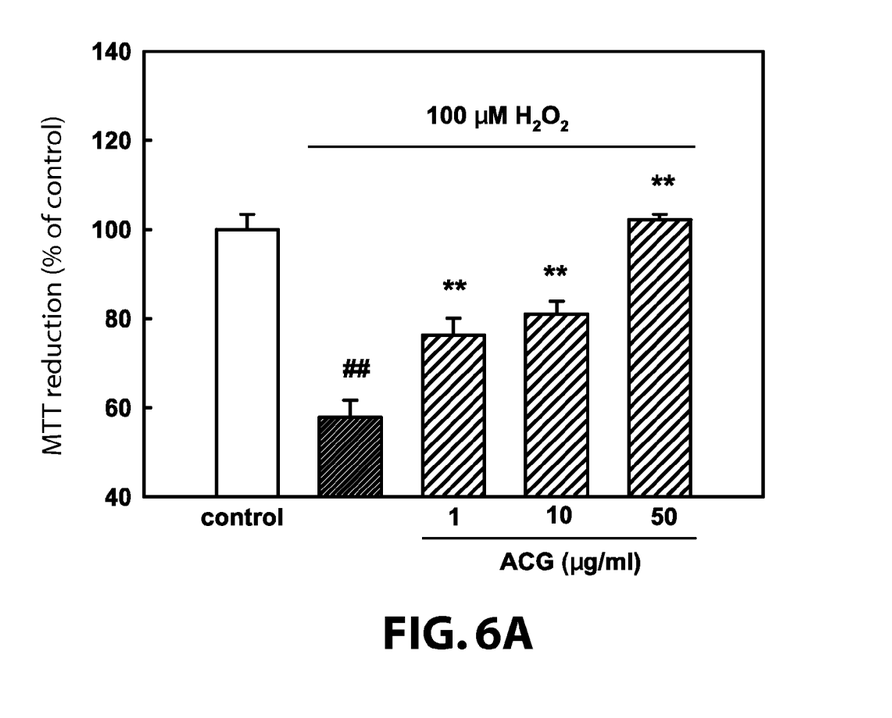
FIG. 6 is a graph showing inhibitory effects of (A) *Aralia elata*, *Chaenomelis Fructus* and *Glycyrrhizae Radix* extract (ACG), (B) *Aralia elata* extract (AE), and (C) *Glycyrrhizae Radix* extract (GR) on $H_2O_2$-induced neuronal death.
Figure 6B:
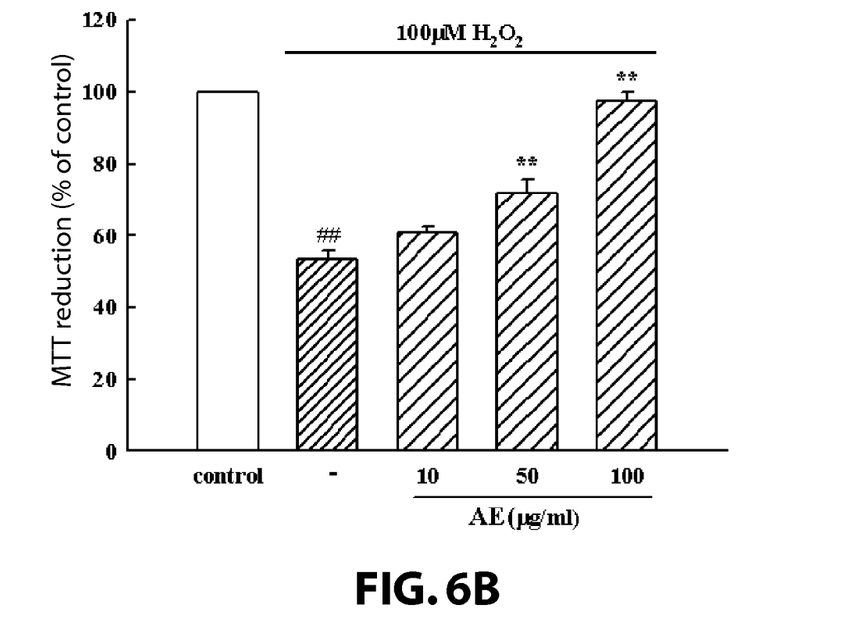
Figure 6C:
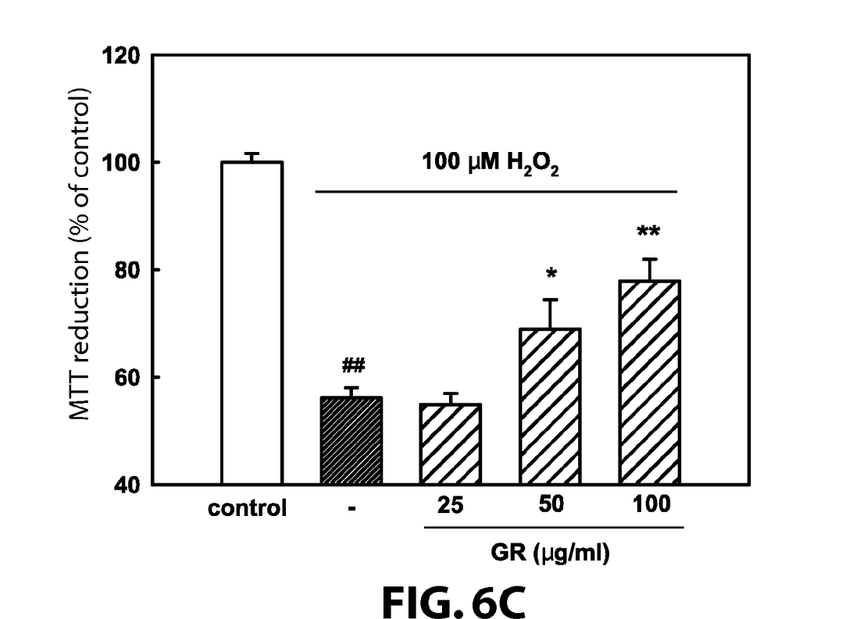

The results are shown in FIG. 6. Referring to FIG. 6(A), compared to the control group (100%), the neuronal cells treated with $H_2O_2$ alone showed cellular apoptosis corresponding to a cell viability of 57.8%, and the neuronal cells administered with ACG, their viability was 76.2% at 1 μg/ml of ACG, 81.0% at 10 μg/ml of ACG, and 102.2% at 50 μg/ml of ACG. From the results, it can be seen that ACG inhibits brain neuronal death by oxidative stress. Meanwhile, inhibitory effects of each component on $H_2O_2$-induced cytotoxicity were tested. *Aralia elata* at a high concentration of 100 μg/ml had an inhibitory effect similar to that of 50 μg/ml of ACG (FIG. 6(B)), *Glycyrrhizae Radix* at a high concentration of 100 μg/ml had a weak inhibitory effect of about 50% (from 56.1% to 80.0%) on apoptosis (FIG. 6(C)), and *Chaenomelis Fructus* had no inhibitory effect on H$_2$O$_2$-induced cytotoxicity. Thus, it was confirmed that by using the combination of *Aralia elata* and *Glycyrrhizae Radix* with *Chaenomelis Fructus* extract having no inhibitory effect on H$_2$O$_2$-induced cytotoxicity separately, a high inhibitory effect on H$_2$O$_2$-induced cytotoxicity is achieved with using much smaller amounts of *Aralia elata* and *Glycyrrhizae Radix* extracts.

(5) Inhibitory Effect of ACG on Glutamate-Induced Neuronal Death

It is known that in degenerative cerebral disorders such as cerebral infarction, glutamate, an excitatory amino acid, is released at a great amount to cause neuronal death. In this experiment, glutamate (500 µM) was added to the cerebral cortex neurons cultured in the experiment (1) and the cells were incubated for 8 hours to investigate an inhibitory effect of ACG on neuronal death.

Figure 7A:
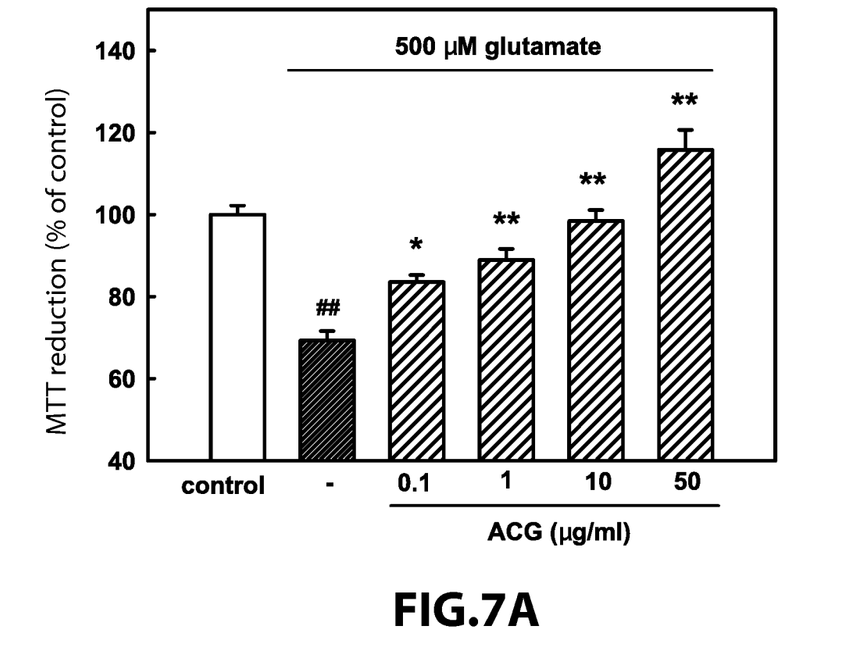
FIG. 7 is a graph showing inhibitory effects of (A) *Aralia elata*, *Chaenomelis Fructus* and *Glycyrrhizae Radix* extract (ACG) and (B) *Aralia elata* extract (AE) on glutamate-induced neuronal death.
Figure 7B:
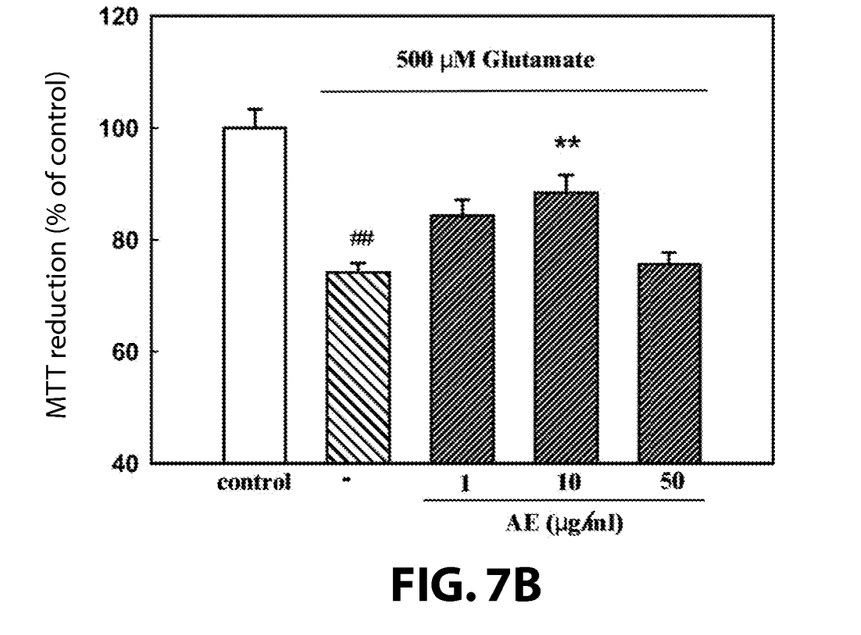
Figure 8A:
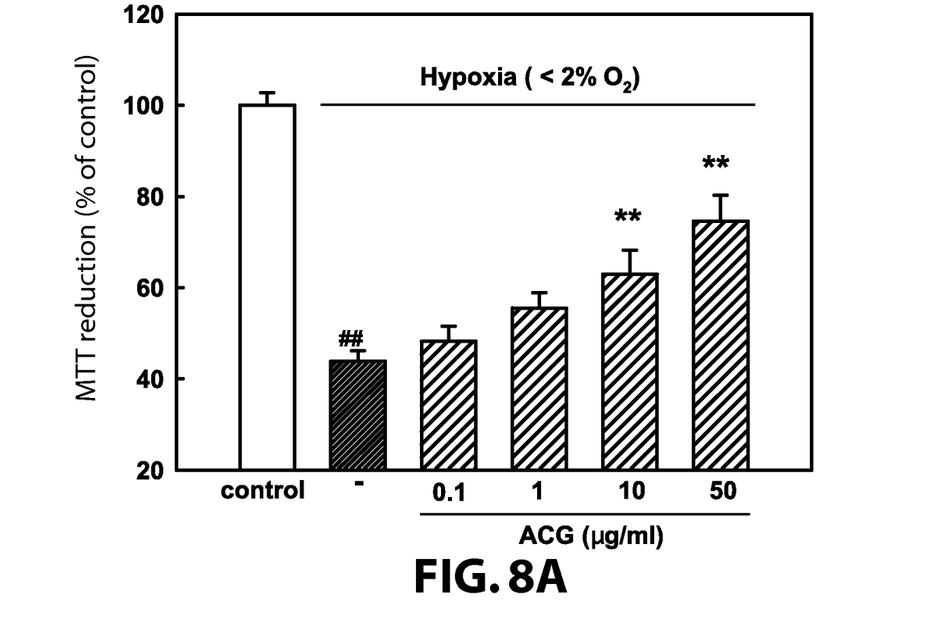
FIG. 8 is a graph showing inhibitory effects of (A) *Aralia elata*, *Chaenomelis Fructus* and *Glycyrrhizae Radix* extract (ACG), (B) *Aralia elata* extract (AE), (C) *Chaenomelis Fructus* extract (CS) and (D) *Glycyrrhizae Radix* extract (GR) on hypoxia-induced neuronal death.
Figure 8B:
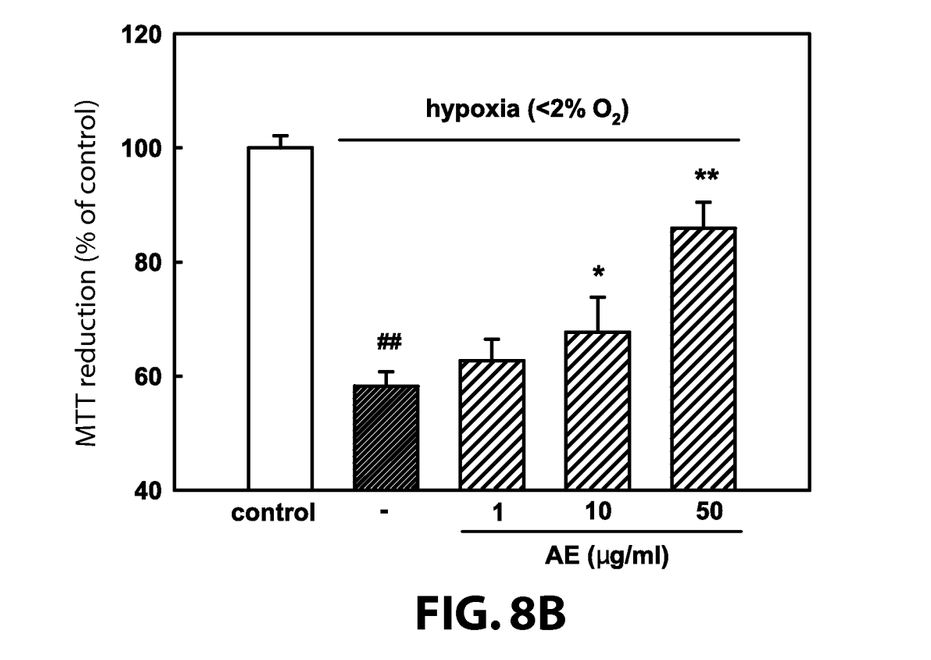
Figure 8C:
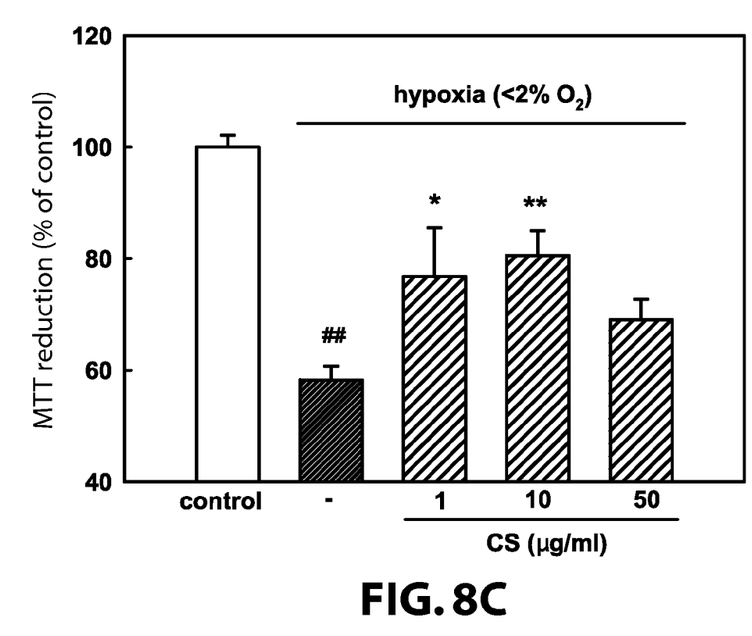
Figure 8D:
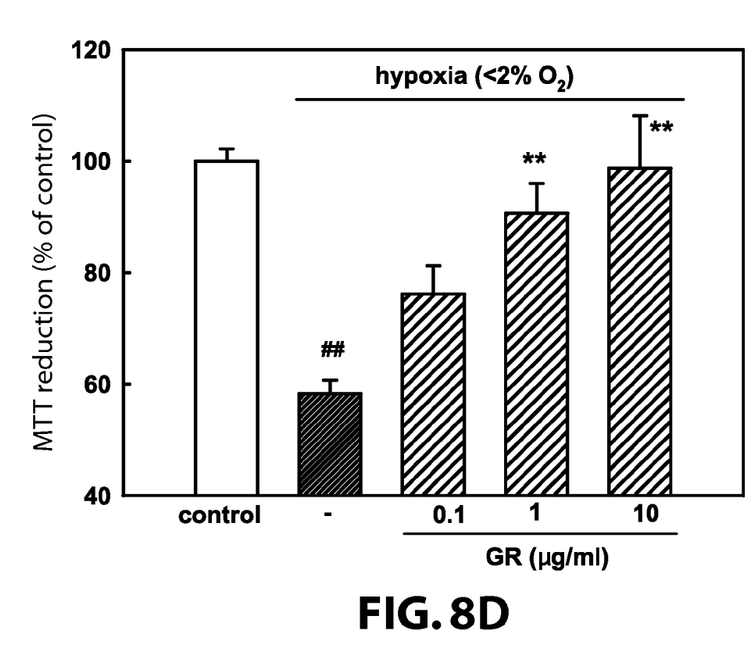
Figure 9A:
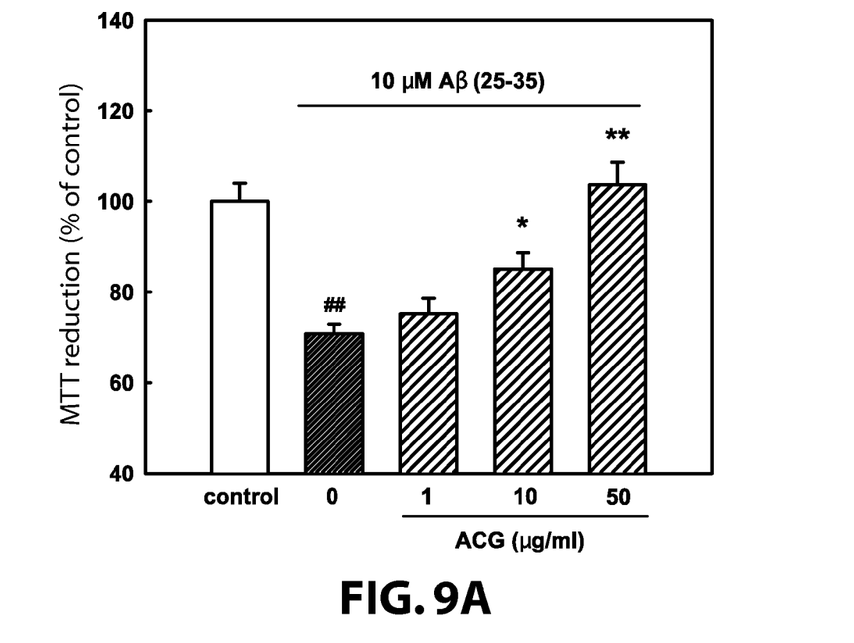
FIG. 9 is a graph showing inhibitory effects of (A) *Aralia elata*, *Chaenomelis Fructus* and *Glycyrrhizae Radix* extract (ACG), (B) *Aralia elata* extract (AE), (C) *Chaenomelis Fructus* extract (CS), and (D) *Glycyrrhizae Radix* extract (GR) on Aβ(25-35)-induced neuronal death.
Figure 9B:
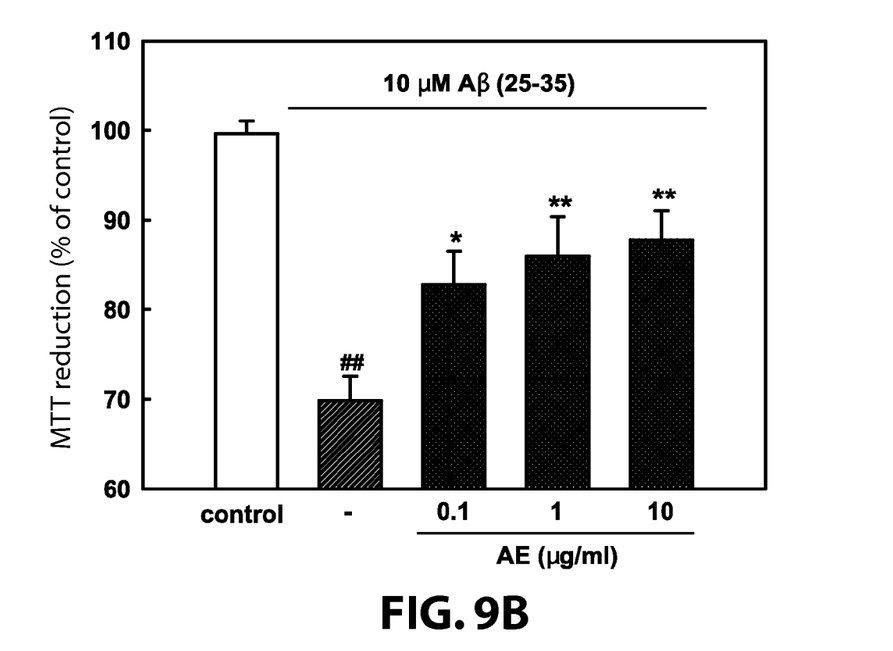
Figure 9C:
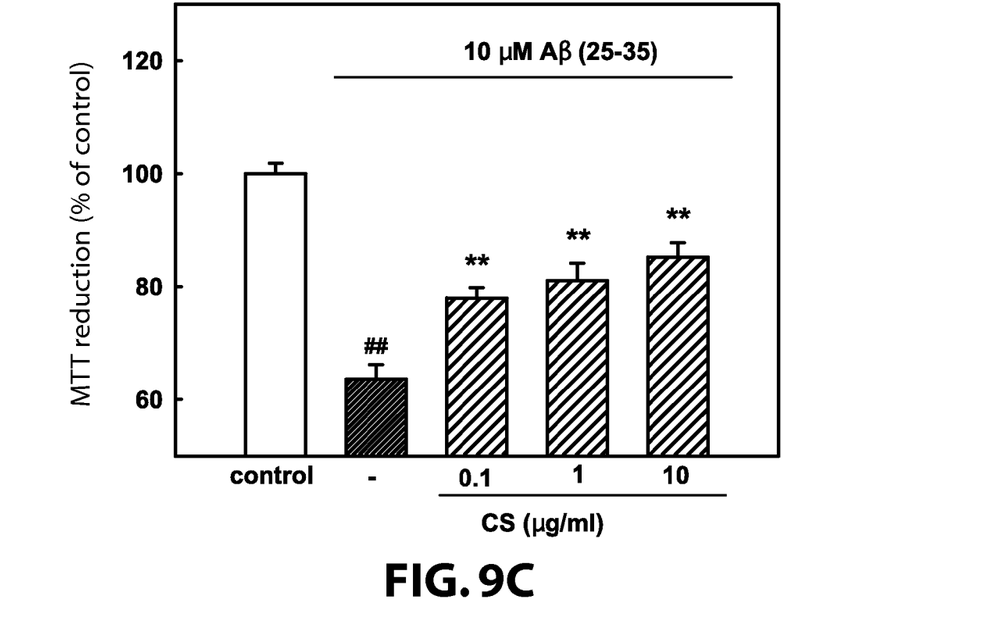
Figure 9D:
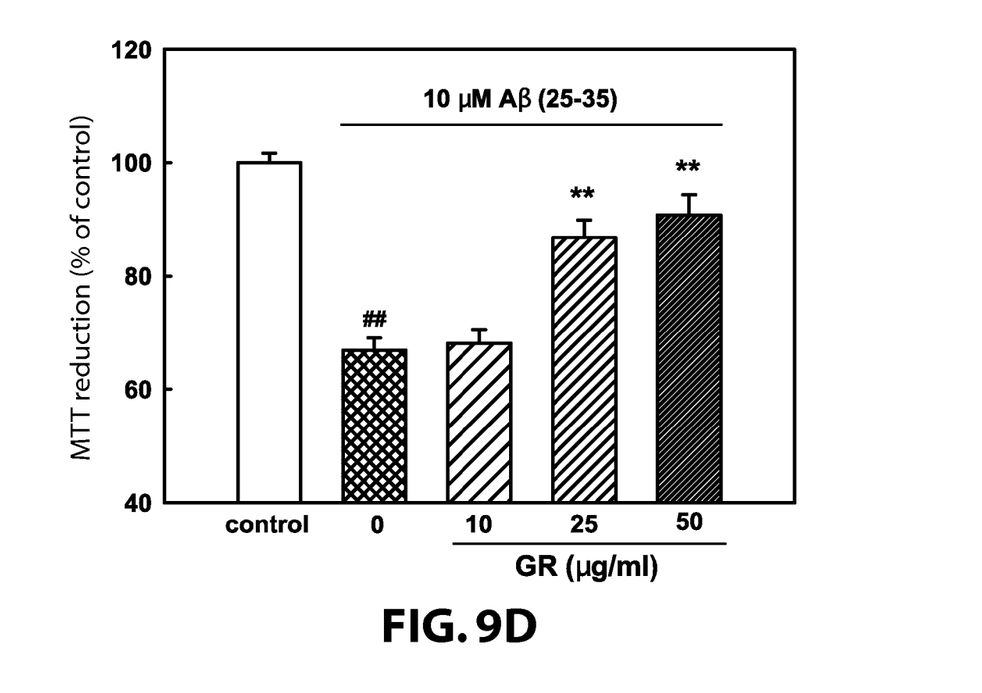

The results are shown in FIG. 7. Referring to FIG. 7(A), compared to the control group (100%), the group treated with glutamate had a viability of 69.3%. Meanwhile, in the group treated with 0.1 µg/ml of ACG, the cell viability was 83.6%; in the group treated with 1 µg/ml of ACG, the cell viability was 88.9%; in the group treated with 10 µg/ml of ACG, apoptosis was almost completely suppressed and the cell viability was 98.4%; and in the group treated with 50 µg/ml of ACG, the cell viability was 115.8% to show that apoptosis under a severe condition of culture in a glucose-free HEPES buffer was suppressed. Thus, it was confirmed that ACG, even at the concentration of as low as 10 µg/ml, completely suppressed glutamate-induced apoptosis. Meanwhile, inhibitory effects of each component were tested. Only *Aralia elata* (AE) at a concentration of 10 µg/ml had a weak inhibitory effect on glutamate-induced cytotoxicity (FIG. 7(B)) and the other components had no inhibitory effect. Thus, it was confirmed that by using the combination of *Aralia elata* extract with *Chaenomelis Fructus* extract and *Glycyrrhizae Radix* extract which have no inhibitory effect on glutamate-induced cytotoxicity separately, a high inhibitory effect on glutamate-induced cytotoxicity is achieved with using a much smaller amount of *Aralia elata* extract.

(6) Inhibitory Effect of ACG on Hypoxia-Induced Neuronal Death

In order to induce ischemia, the cultured cerebellum granule cells used in the experiment (2) were incubated in a chamber under hypoxia to induce apoptosis and an inhibitory effect of ACG on the apoptosis was investigated. That is, after culture of the cerebellum granule cells for five to seven days in cytosine arabinoside-containing culture medium, the medium was exchanged with a glucose-free HEPES buffer and then, the well plates were placed in a hypoxia chamber in which 2% O$_2$, 5% CO$_2$, and 93% N$_2$ were maintained, and the incubation was performed in the chamber for 24 hours. Then, the medium was exchanged with a serum-free DMEM, and then the incubation was further performed in a 5% CO$_2$ incubator for 6 hours and the cell viability was measured by MTT assay. As the control group, cells in a serum-free DMEM and glucose-free HEPES buffer were placed in the 5% CO$_2$ incubator for the same time period.

The results are shown in FIG. 8. Referring to FIG. 8(A), the cell viability under hypoxia was 43.6%, and in the group administered with 1, 10, and 50 µg/ml of ACG, the brain cell viability was 55.6, 63.0, and 74.6%, respectively. That is, ACG suppressed hypoxia-induced apoptosis in a dose-dependent manner. Meanwhile, inhibitory effects of each component were tested. *Aralia elata* at a high concentration of 50 µg/ml had an inhibitory effect similar to that of 50 µg/ml of ACG (FIG. 8(B)), *Chaenomelis Fructus* at a concentration of 10 µg/ml had a weak inhibitory effect (FIG. 8(C)), and *Glycyrrhizae Radix* had a high inhibitory effect at a concentration of 10 µg/ml. The inhibitory effect of *Glycyrrhizae Radix* on hypoxia-induced neuronal death has not been known at all, and it was confirmed that by using the combination of *Aralia elata* and *Chaenomelis Fructus* which had a small inhibitory effect with *Glycyrrhizae Radix* which has a high inhibitory effect, a high inhibitory effect is achieved.

(7) Inhibitory Effect of ACG on Aβ(25-35)-Induced Neuronal Death

The above Experimental Example 2 showed that the administration of Aβ(25-35) to the ventricle of a mouse induced memory impairment, and in the groups orally administered with ACG for a certain period of time, memory impairment was suppressed. This experiment was performed to reveal the related biochemical mechanism for the same. Cerebral cortex neuronal cells were cultured and treated with 10 µM Aβ(3 (25-35) to induce apoptosis and an inhibitory effect of ACG on the Aβ(25-35)-induced apoptosis was investigated.

The results are shown in FIG. 9. Referring to FIG. 9, in the group treated with 10 µM Aβ(25-35), compared to the control group (100%), the cell viability was 70.2%, and in the group further treated with 1, 10, and 50 µg/ml of ACG, the viability was restored to 75.2, 85.1, and 103.6%, respectively (FIG. 9(A)). Regarding inhibitory effects of each component on 10 µM Aβ(25-35)-induced cytotoxicity, *Aralia elata* (AE) and *Chaenomelis Fructus* (CS) had a small inhibitory effect at a concentration of 10 µg/ml, but caused serious toxicity at a concentration higher than 10 µg/ml. *Glycyrrhizae Radix* had a high inhibitory effect at a concentration of 25 and 50 µg/ml (FIG. 9(B), (C) and (D)). The inhibitory effect of *Glycyrrhizae Radix* on Aβ-induced neuronal death has not been known at all, and it was confirmed that by using the combination of *Aralia elata* and *Chaenomelis Fructus* having a low inhibitory effect and causes serious toxicity at a certain concentration or higher with *Glycyrrhizae Radix*, a high inhibitory effect is achieved.

From the results, it was confirmed that the mixed extract from *Aralia elata, Chaenomelis Fructus* and *Glycyrrhizae Radix* is effectively used as a prophylactic or therapeutic agent for cerebrovascular disorders such as cerebral infarction, cerebral ischemia, stroke, or vascular dementia.

According to the present invention, an ethanol extract from *Aralia elata, Chaenomelis Fructus*, and *Glycyrrhizae Radix* substantially reduces infarct and edema volumes in rat ischemia, effectively suppresses memory impairment in a mouse model with Aβ-induced memory impairment, and effectively suppresses death of cultured neuronal cells induced by hydrogen peroxide, glutamate, an excitatory amino acid, hypoxia, and Aβ. In particular, it is an unexpected finding that *Aralia elata, Chaenomelis Fructus*, and *Glycyrrhizae Radix* have complementary actions by supplementing a mechanism deficient to the other components one another, and due to the complementary actions, the combination thereof shows remarkably synergic effect. Accordingly, the ethanol extract from *Aralia elata, Chaenomelis Fructus*, and *Glycyrrhizae Radix* according to the present invention may effectively protect neuronal cells, effectively prevent and treat cerebral infarction, cerebral edema, cerebral ischemia, and vascular dementia, and effectively improve memory impairments, without any side effect.

What is claimed is:

1. A composition comprising, as an active ingredient, an ethanolic extract from *Aralia elata*, an ethanolic extract from *Chaenomelis Fructus*, and an ethanolic extract from *Glycyrrhizae Radix*, wherein the extracts are in amounts effective for treating cerebral infraction, cerebral edema, cerebral ischemia, vascular dementia, memory impairment, or protecting neuronal cells.

2. The composition of claim 1, wherein the ethanolic extracts from *Aralia elata, Chaenomelis Fructus*, and *Glycyrrhizae Radix* are obtained by mixing *Aralia elata, Chaenomelis Fructus*, and *Glycyrrhizae Radix* and extracting the mixture with ethanol, or by extracting each of *Aralia elata, Chaenomelis Fructus*, and *Glycyrrhizae Radix* with ethanol and combining the extracts.

3. The composition of claim 1, wherein a weight ratio of the *Aralia elata, Chaenomelis Fructus*, and *Glycyrrhizae Radix* extracts is 0.5 to 2:0.5 to 2:0.5 to 2.

4. The composition of claim 3, wherein a weight ratio of the *Aralia elata, Chaenomelis Fructus*, and *Glycyrrhizae Radix* extracts is 1:1:1.

5. The composition of claim 1, wherein the extract of *Aralia elata* is obtained from is the whole plant or an edible shoot.

6. The composition of claim 1, wherein the composition is an oral dosage form.

7. A method of treating cerebral infraction, cerebral edema, cerebral ischemia, vascular dementia, memory impairment, or of protecting neuronal cells, comprising administering to a patient in need thereof an effective amount of the composition according to claim 1.

8. The method of claim 7, wherein the ethanolic extracts from *Aralia elata, Chaenomelis Fructus*, and *Glycyrrhizae Radix* are obtained by mixing *Aralia elata, Chaenomelis Fructus*, and *Glycyrrhizae Radix* and extracting the mixture with ethanol, or by extracting each of *Aralia elata, Chaenomelis Fructus*, and *Glycyrrhizae Radix* with ethanol and combining the extracts.

9. The method of claim 7, wherein a weight ratio of the *Aralia elata, Chaenomelis Fructus*, and *Glycyrrhizae Radix* extracts is 0.5 to 2:0.5 to 2:0.5 to 2.

10. The method of claim 9, wherein a weight ratio of the *Aralia elata, Chaenomelis Fructus*, and *Glycyrrhizae Radix* extracts is 1:1:1.

11. The method of claim 7, wherein the *Aralia elata* extract is obtained from the whole plant or an edible shoot.

* * * * *